(12) United States Patent
Faxides

(10) Patent No.: US 7,368,060 B2
(45) Date of Patent: May 6, 2008

(54) APPARATUSES AND METHODS FOR DETECTING CONTAMINANT IN A FUEL SYSTEM

(75) Inventor: Mihalis Faxides, Neo Rysio (GR)

(73) Assignee: Warning SA, Thessaloniki (GR)

( * ) Notice: Subject to any disclaimer, the term of this patent is extended or adjusted under 35 U.S.C. 154(b) by 470 days.

(21) Appl. No.: 11/035,474

(22) Filed: Jan. 14, 2005

(65) Prior Publication Data

US 2006/0157421 A1    Jul. 20, 2006

(51) Int. Cl.
*B01D 17/12* (2006.01)

(52) U.S. Cl. .................... 210/744; 210/86; 210/94; 210/472; 210/533; 210/539

(58) Field of Classification Search .............. 210/85, 210/86, 94, 312, 313, 533, 540, 744, 746, 210/803, 472, 539
See application file for complete search history.

(56) References Cited

U.S. PATENT DOCUMENTS

| | | | | |
|---|---|---|---|---|
| 2,488,009 A | * | 11/1949 | Goebel | 210/308 |
| 3,122,501 A | * | 2/1964 | Hultgren | 210/94 |
| 3,237,770 A | * | 3/1966 | Humbert, Jr. | 210/94 |
| 4,010,101 A | * | 3/1977 | Davey | 210/86 |
| 4,276,161 A | | 6/1981 | Matsui et al. | |
| 4,488,970 A | * | 12/1984 | Clark | 210/746 |
| 4,562,431 A | | 12/1985 | Jahnke et al. | |
| 4,619,764 A | | 10/1986 | Church et al. | |
| 4,624,779 A | * | 11/1986 | Hurner | 210/180 |
| 5,213,682 A | | 5/1993 | Richardson | |
| 6,207,045 B1 | * | 3/2001 | Jiang | 210/86 |
| 6,423,213 B1 | * | 7/2002 | Mazurek | 210/115 |

FOREIGN PATENT DOCUMENTS

| | | |
|---|---|---|
| DE | 37 40 804 | 7/1989 |
| EP | 0 715 873 | 12/1996 |
| GB | 2 065 336 | 6/1981 |
| GB | 2 121 187 | 12/1983 |
| GB | 2 140 319 | 11/1984 |
| WO | WO 01/33069 | 5/2001 |

* cited by examiner

*Primary Examiner*—Matthew O. Savage
(74) *Attorney, Agent, or Firm*—Ward and Smith, P.A.

(57) ABSTRACT

Apparatuses and methods are provided for detecting contaminant in a fuel system, such as a fuel system of an internal combustion engine. The apparatus includes a fuel filter comprising an upper unit having a fuel inlet port, a fuel outlet port, and a closeable vent port and a lower unit releasably mounted to the upper unit and comprising a contaminant collection zone adapted for holding collected contaminant and a closable contaminant outlet port adapted for draining the collected contaminant. The apparatus further includes a programmable low-voltage variable contaminant detection sensor formed integrally within the upper unit of the fuel filter and comprising detection probes extending into the lower unit of the fuel filter for sensing contaminant levels within the contaminant collection zone, the sensor being adapted for generating a signal upon detection of a predetermined level of contaminant in the contaminant collection zone. The apparatus further includes at least one indicator for producing an alarm condition in response to receiving the signal from the contaminant detection sensor.

18 Claims, 3 Drawing Sheets

APPARATUSES AND METHODS FOR DETECTING CONTAMINANT IN A FUEL SYSTEM

TECHNICAL FIELD

The subject matter disclosed herein relates generally to fuel systems, and more particularly to providing apparatuses and methods for detecting and removing contaminants in a fuel system of an internal combustion engine or the like.

BACKGROUND ART

The fuel for use in internal combustion engines and heating systems is usually filtered before being fed to the engine or heating system. Filters are necessary because the presence of contaminants, such as water, in fuel systems has been found to be particularly disadvantageous for running efficiency of the machine that is using the fuel. For instance, as in the case with diesel or gasoline engines in boats or land vehicles, the presence of water in the fuel may cause corrosion of the fuel injector system with consequent reduction of the efficiency thereof and eventual complete breakdown thereof. Additionally, water in fuel systems may present a dangerous situation when power from an engine is necessary and water in the fuel results in the inability to deliver power at a crucial point in the operation of the engine.

In the past, various types of conventional fuel filters have been used in order to separate and/or remove water from the fuel prior to feeding the engine. These conventional fuel filters typically include a casing made of glass or steel that is mounted underneath a bracket having a fuel inlet and a fuel outlet and a filter element that is accommodated within the casing. The fuel introduced from the fuel inlet flows down a central passageway and enters the casing through a lower opening. The fuel changes flow direction to ascend in the casing and is filtered by the filter element and sent to the engine through the fuel outlet. In these conventional fuel filters, a major part of the water content included in the fuel may fall by gravity when the fuel flows from the opening. When the fuel is reversed in direction to flow upwardly, the remainder of the water content may attach to the surface of the filter element and accumulate to form droplets, which fall and gather in the bottom of the casing. A very small amount of water may pass through the filter element but such a small amount of water is very easily fully burned in the engine and typically does not affect engine efficiency. The water gathering in the bottom part of the casing may be removed at a suitable maintenance interval.

Drawbacks have been found in such conventional fuel filters. For instance, since a large amount of water may attach to the surface of the filter element and accumulate thereon when the filter is in use, the surface of the filter element applied with water gathering treatment or water repellant treatment is gradually attacked by the water over a period of time so that the life of the filter element is shortened. Furthermore, as a recent requirement especially related to exhaust gas purification, it is necessary to remove the water in the fuel to substantially zero in order to accurately maintain the measuring of the fuel amount at the fuel injection valve. From this requirement, it is necessary to separate the water content in the fuel as completely as possible before reaching the filter element.

An additional disadvantage to conventional fuel filters has been realized in regards to the water content accumulated in the bottom part of the casing of the fuel filter that has had to be manually removed at certain regular intervals. It has been found that if the water removing process is forgotten, the water level may reach the lower surface of the filter element wherein not only does the filter efficiency deteriorate but a large amount of water may be sent to the engine together with the fuel. This has an especially detrimentally effect when the filter element is old and the filtering function has deteriorated wherein the water sent to the engine may cause rust to be introduced into the fuel injection system or may lead to other major efficiency decreases in engine production.

In light of these drawbacks of conventional fuel filtering systems, various apparatuses have been designed to attempt to resolve these negative characteristics by alerting the user of the presence of water and/or automatically draining collected water from the fuel system.

U.S. Pat. No. 4,276,161 to Matsui et al. discloses a fuel filter with a water level detector having an electrode provided at a bottom part of the casing of the fuel filter forming a detecting gap with the metal body of the casing. The sensor responds to water level in the casing so that should the water level in the casing of the fuel filter reach a predetermined level, a low resistance condition between the electrode and casing is detected by a water level detecting circuit. The sensor of Matsui et al. requires a strong current passing through the sensor and is a passive sensor that does not allow programmability of the water level for use with varying types of fuel systems or machines.

U.S. Pat. No. 4,562,431 and corresponding U.K. Patent Application No. GB 2,121,187 to Jahnke et al. disclose a motor fuel filter equipped for water separation by interrupting or greatly reducing the current passing through the sensor after the sensor has given a signal indicating the presence of water in sufficient quantity to require draining soon. The sensor system of Jahnke et al. is a passive system that does not allow for water level threshold programmability for the use with varying types of fuel systems.

U.S. Pat. No. 4,619,764 to Church et al. is directed to a filter assembly and associated filter unit including a repelling action filter media for use in vacuum or suction side fuel filter applications. The filter unit is a screw-on unit with centrally located threads at opposite ends of the filter unit and with a specifically designed end cap allowing use of the filter unit with a dual zone collection bowl normally used for coalescing pressure side filter applications. The end cap includes holes which allows use of both of the collection zones in spite of the normal isolation between the collection zones. The sensor disclosed in Church et al. is a passive level sensor that does not allow for variable water level threshold programmability.

U.S. Pat. No. 5,213,682 to Richardson discloses a fuel supply system including a probe device mounted in an outlet passage of a filter head and having probe elements extending into a filter unit which is removably engaged with the head. Also disclosed is circuitry in the device responsive to contact with water in the filter to complete a circuit and actuate a signal to indicate the presence of such water. The water detection sensor of Richardson is installed in a standard fuel filter and is related to a passive water detection system that does not allow variable programmability of threshold water levels.

U.K. Patent Application No. GB 2,065,336 to Mackenzie is directed to a device for discharging water and/or air contaminant from a mineral oil contaminant separator or from a mineral oil reservoir and separator having such a device. This system includes a vent valve or pump that is automatically opened when a first probe detects the presence of contaminant and which remains open for a prescribed time after the contaminant is cleared. A second probe is provided which gives an alarm indication and that also energizes the motor valve that may operate for a longer period than the first valve. The sensors disclosed in Mackenzie are asymmetrical and are passive sensors that do not allow for variable programmability of water level thresholds.

European Patent Application No. EP 0715873 to Biere et al. discloses a fuel/water separator including an all sheet metal shell having a bottom which is secured to a metal adaptor plate enabling a drain valve and a water detector to be attached to the bottom of the shell. The sensors disclosed in Biere et al. are utilized with metallic filter elements and do not allow for the variable programmability of water level thresholds.

Finally, PCT Application No. WO 01/33069 to Girondi is directed to a unit for automatically bleeding off water which separates in a vehicle fuel filter wherein the unit comprises a sensor means positioned in the collection chamber to undergo activation when the water level reaches a predetermined maximum value. There is also provided an electrically operated withdrawal device connected to the vehicle electrical system to withdraw the water separated within the collection chamber through the bleed outlet or to close the outlet. A microprocessor is also provided connected to the sensor means and to the switch means of the vehicle electrical power system, to electrically power the withdraw device when the sensor means is activated and the ignition key is in a first activation position. The sensor disclosed in Girondi utilizes a flow mechanism for activating the withdraw device at a certain level. This sensor system does not allow for the variable programmability of water level thresholds determined by a probe system.

The prior art fuel filter alarm systems have numerous disadvantages. For instance, the sensor systems of prior art devices have not allowed for the contaminant level of varying thresholds to be readily changed depending on the size engine utilizing the fuel filter system. Mainly, the fuel filter systems of the prior art have had to be designed specifically for varying sized engines that can accommodate varying levels of water contamination. This has required that dealers stock numerous sizes of the fuel filter sensor mechanisms in order to satisfy all customer requirements. Additional disadvantages of prior art systems have included the placement of the fuel filter apparatuses in disadvantageous locations within the engine that prevent the user from approaching the fuel filter and/or removing the water within the fuel filter. Another disadvantage is that while some prior art devices warn about the existence of water, they do not readily offer the capability for water removal which can result in the malfunction of the engine.

As such, there remains the need for the creation of a contaminant detection system for use in fuel systems of internal combustion engines, heating systems, and the like wherein the unit can be placed easily between the fuel reservoir and the engine, the unit can give the capability of warning about the existence of water or other contaminant in the fuel, and can also allow the removal of the contaminant with only temporary pause of the operation of the engine.

There additionally remains the need for a programmable variable sensor system that can be readily preprogrammed to varying levels of contaminant or water levels that would allow the deployment of the same water sensing circuit with fuel filter systems developed for different sized engines where the capacity of the fuel filter can differ significantly.

SUMMARY

According to one embodiment of the present subject matter, an apparatus for detecting contaminant in a fuel system is provided wherein the apparatus comprises a fuel filter comprising an upper unit having a fuel inlet port, a fuel outlet port, and a closeable vent port and wherein the fuel filter further comprises a lower unit releasably mounted to the upper unit and comprising a contaminant collection zone adapted for holding collected contaminant and a closeable contaminant outlet port adapted for draining the collected contaminant. The contaminant detecting apparatus further comprises a programmable low voltage variable contaminant detection sensor formed integrally within the upper unit of the fuel filter and comprising detection probes extending into the lower unit of the fuel filter for sensing contaminant levels within the contaminant collection zone, the sensor being adapted for generating a signal upon detection of a predetermined level of contaminant in the contaminant collection zone. The apparatus further comprises at least one indicator for producing an alarm condition in response to receiving the signal from the contaminant detection sensor wherein the indicator may comprise a visual indicator capable of producing a visual alarm condition or may comprise an audible indicator capable of producing an audible alarm condition.

A method is also provided for detecting contaminant in a fuel system of an internal combustion engine. The method generally comprises providing a contaminant detection apparatus as described herein above, placing the contaminant detection system between a fuel source and the internal combustion engine and programming the contaminant detection system with the predetermined level of contaminant desired for generation of the alarm signal. The method further comprises causing fuel to enter the contaminant detection apparatus from the fuel source, monitoring the fuel and generating the alarm signal once the predetermined level of contaminant in the contaminant collection zone is reached. An alarm condition is indicated upon receipt of the alarm signal and upon indication of the alarm condition the method further comprises opening the upper unit vent port and the lower unit contaminant outlet port to cause draining of the collected contaminant and closing the upper vent port and the lower unit contaminant outlet port upon draining of all of the collected contaminant.

It is therefore an object to provide apparatuses and methods for detecting contaminant in a fuel system wherein the detection of the contaminant is programmably variable by the user.

An object of the present subject matter having been stated hereinabove, and which is addressed in whole or in part by the present subject matter, other objects will become evident as the description proceeds when taken in connection with the accompanying drawings as best described hereinbelow.

DETAILED DESCRIPTION

Figure 1:
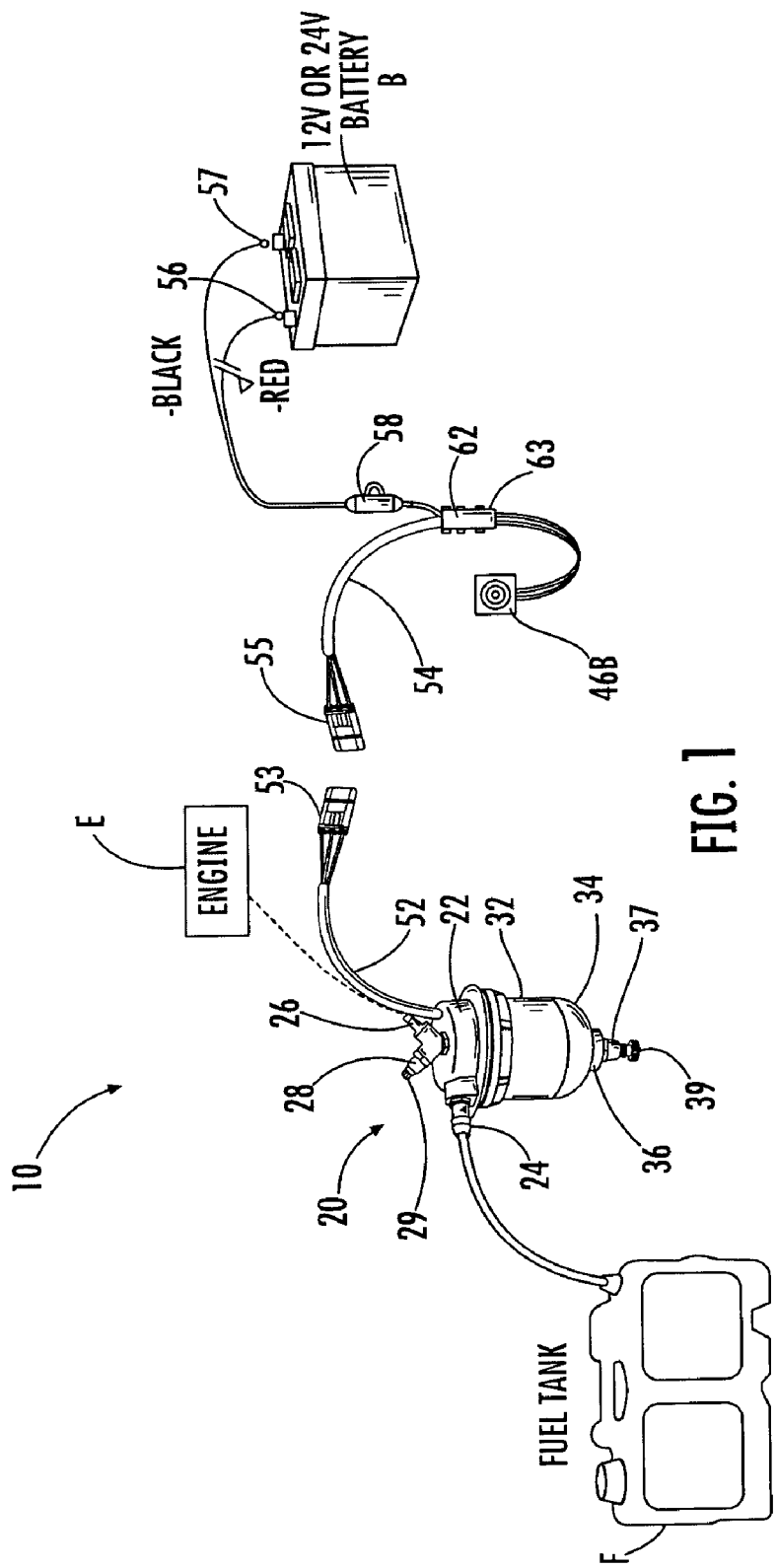
FIG. 1 is a perspective view of the overall fuel system of an engine incorporating the contaminant detection apparatus provided in accordance with the subject matter disclosed herein.

Referring now to FIG. 1, a fuel system incorporating a preferred embodiment of the contaminant detection apparatus of the present subject matter is shown. The fuel system includes a fuel source F that supplies fuel to engine E for the powering of an attached machine, wherein the fuel supplied by fuel source F may consist of gasoline, diesel or any other type of petroleum product. It is understood that engine E may comprise an internal combustion engine for powering a vehicle such as a marine craft or land vehicle, may comprise a burner system for heating applications, or may comprise any other application that utilizes petroleum products. A preferred embodiment of an apparatus for detecting contaminant in the fuel being fed from fuel source F is shown generally as 10 and is positioned in operative connection between fuel source F and engine E. The placement of contaminant detection apparatus 10 allows for the detection and/or removal of contaminant in the fuel prior to the contaminated fuel reaching engine E. With such placement, the contaminant destruction of other fuel system parts of engine E, such as the injection system and the like, is minimized. While the most often cited contaminant in fuel systems is water, it is understood that the present subject matter may be directed to detecting any other contaminants found in fuels.

Figure 2:
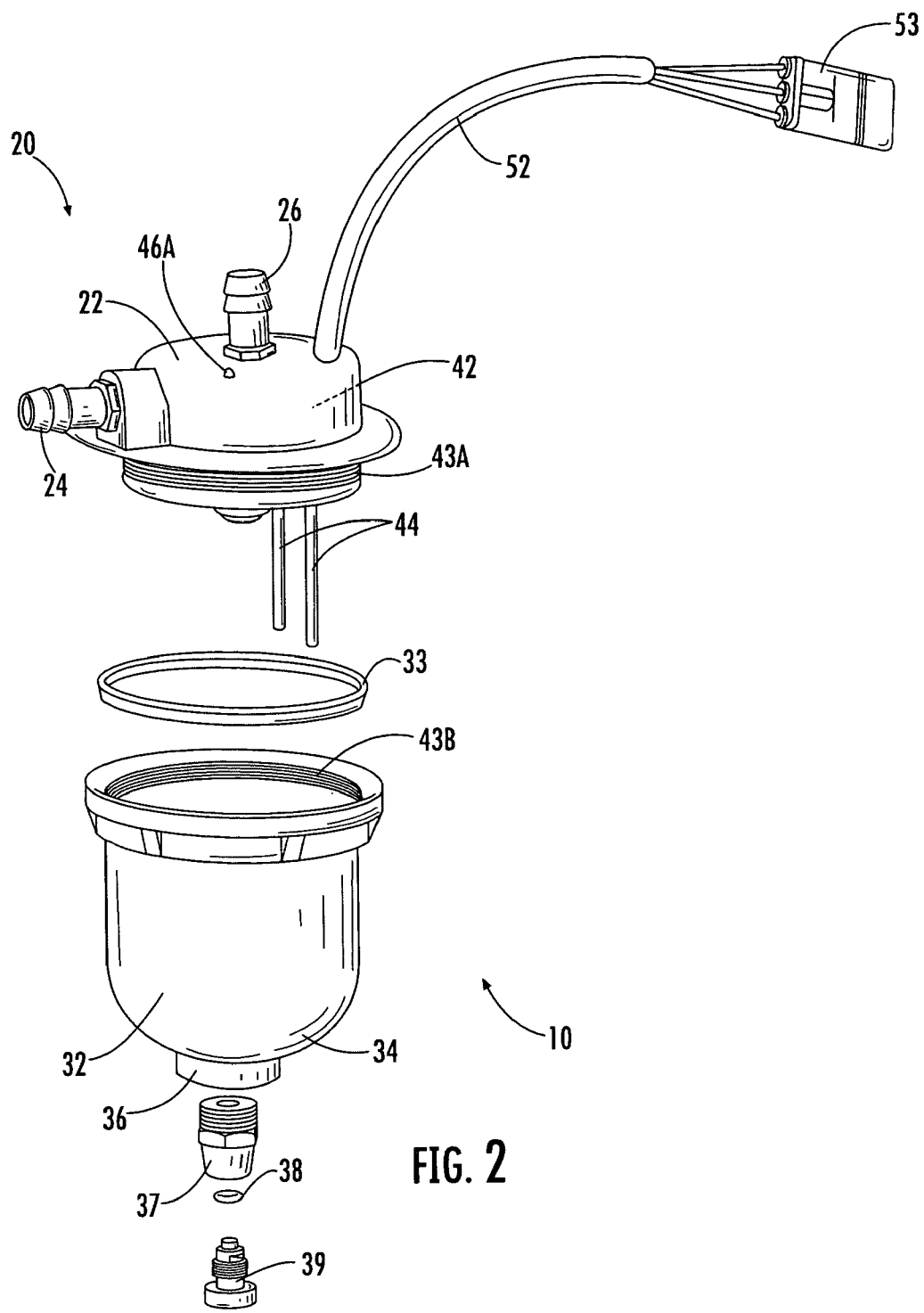
FIG. 2 is a perspective exploded view of an embodiment of a contaminant detection apparatus providing in accordance with the subject matter disclosed herein.
Figure 3:
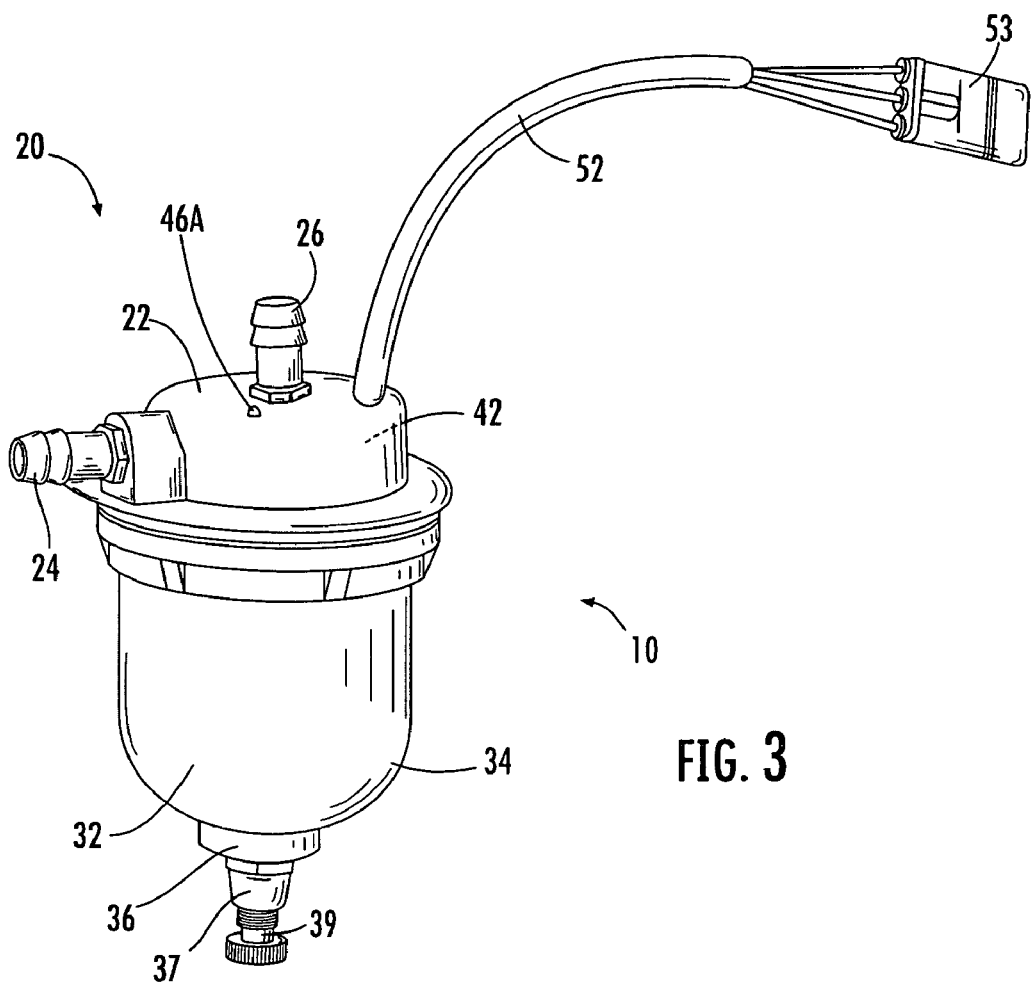
FIG. 3 is a perspective assembled view of the contaminant detection apparatus illustrated in FIG. 2.

With reference to FIG. 1 and with further reference to FIGS. 2 and 3, contaminant detection apparatus 10 comprises a fuel filter unit shown generally as 20. Fuel filter unit 20 comprises an upper unit 22 and a lower unit 32 and may house a fuel filter element (not shown) of any type known to those of skill in the art.

Upper unit 22 is preferably constructed of a metal material and includes a fuel inlet port 24 for the receiving of fuel from fuel source F and also includes a fuel outlet port 26 wherein fuel exits fuel filter unit 20 and is fed to engine E. Upper unit 22 may further include a closeable vent port 28 (shown in FIG. 1) for the releasing of vacuum within fuel filter unit 20 during draining of contaminant from the unit. Closeable vent port 28 may consist of a screw-type valve 29 or any other vent valve known to those of skill in the art.

Lower unit 32 is preferably generally cylindrical and concave in nature and is releasably mounted to upper unit 22 by means of screw threads 43A, 43B or the like, wherein the engagement between upper unit 22 and lower unit 32 is sealed by an O-ring 33. This mounting allows lower unit 32 to be removed readily for service of the inside of the unit or for replacement of the enclosed fuel filter element (not shown). Lower unit 32 further comprises a contaminant collection zone 34 adapted from holding collected contaminant after it has been separated from the fuel and settles. A closeable contaminant outlet port 36 is located on the lowest surface of contaminant collection zone 34 and is adapted for draining the collected contaminant. Closeable contaminant outlet port 36 may include a post portion 37 and a screw portion 39 that is matingly engaged with post portion 37 and is sealed with the intervention of an O-ring 38. In order for a user to quickly gauge the amount of contaminant present in contaminant collection zone 34, lower unit 32 is preferably constructed of a translucent material such as clear plastic or similar material.

Contaminant detection apparatus 10 further comprises a programmable low-voltage variable contaminant detection sensor 42, which is formed integrally within fuel filter upper unit 22 via a hermitically sealing method or other sealing methods known to those of skill in the art. Contaminant detection sensor 42 further comprises one or more detection probes 44 that extend into fuel filter lower unit 32 for sensing contaminant levels within contaminant collection zone 34. Contaminant detection sensor 42 measures the resistance variation in the fuel caused by the presence of water or other contaminants and is capable of determining when the resistance moves below a certain predetermined threshold level. Detection probes 44 are continuously under voltage, that voltage typically being a low-voltage such as 5V that cannot inhibit sparking within the fuel source. Contaminant detection sensor 42 utilizes a microprocessor incorporating a software program detection algorithm which is capable of varying levels of programmability by the user. As such, the same contaminant detection sensor 42 can be used with different capacity fuel filter units 20 and is capable of detecting varying thresholds of contaminant accumulation within contaminant collection zone 34. Therefore, one particular contaminant detection sensor 42 may be used with different sized engines E where the capacity of fuel filter unit 20 can differ significantly.

Contaminant detection sensor 42 is constantly monitoring fuel flowing through fuel filter unit 20 through the use of detection probes 44 and is adapted to generate a signal, such as an alarm signal, upon the detection of a predetermined level of contaminant in contaminant collection zone 34. Contaminant detection apparatus 10 further comprises at least one indicator for producing an alarm condition in response to receiving this signal from contaminant detection sensor 42. This indicator may comprise a visual indicator 46A capable of producing a visual alarm condition such as changing from a green color to a red color when the content of contaminant in contaminant collection zone 34 exceeds a predetermined level, or may comprise an audible indicator 46B capable of producing an audible alarm condition when such level is exceeded. These indicators 46A, 46B may be placed on or near fuel filter unit 20 or may be placed close to the vehicle's user, such as at a helm position on a marine vehicle. The incorporation of indicators 46A, 46B into contaminant detection apparatus 10 allows the user to not have to constantly monitor fuel filter unit 20 itself, but alerts the user when contaminant in the fuel has reached a threshold level and requires draining.

The electronic components of contaminant detection apparatus 10 are powered by a battery B, such as a 12 volt or 24 volt battery power source. The electrical components are connected to battery B via cables such as cable tresses 52, 54 and connection plugs 53, 55. Cables 52, 54 are connected to battery B via positive terminal 56 under mechanical voltage (e.g. resolution counter) and negative terminal 57. Between positive terminal 56 and connection plug 55 of cable 54, there may be a safety case 58, such as a fuse.

As an example of the operation of contaminant detection apparatus 10 for the detection of contaminant, such as water, in the fuel system of an internal combustion engine E, the user will first provide a contaminant detection apparatus 10 as described hereinabove. Contaminant detection apparatus 10 will be placed in between fuel source F and engine E. The user will then program contaminant detection sensor 42 with the predetermined level of contaminant desired for generation of the alarm signal. For example, contaminant detection sensor 42 may be programmed to generate an alarm signal when the concentration of water in contaminant collection zone 34 reaches a concentration of 20%. The predetermined level of contaminant may vary with the engine size or type as various engines are capable of functioning efficiently with various levels of contaminant in the fuel.

Once the predetermined contaminant threshold has been programmed, the user may cause fuel to enter fuel filter 20 of contaminant detection system 10, most probably by starting of engine E. As fuel flows through the system, detection probes 44 of contaminant detection sensor 42 are constantly monitoring the accumulation of contaminant in contaminant collection zone 34. Once the predetermined level of contaminant in contaminant collection zone 34 is reached, contaminant detection sensor 42 will generate an alarm signal which will then be received by indicators 46A, 46B which will subsequently generate an alarm condition. For example, if the user has pre-programmed contaminant detection sensor 42 to generate an alarm signal when the level of water in the fuel reaches 20%, once the water level reaches this percentage an alarm signal will be generated which in turn will cause indicator 46A, 46B to produce an alarm condition (visual and/or audible) thus alerting the user that the critical contaminant threshold has been reached and the unit should be drained.

Upon notification of the alarm condition, the user will temporarily cause fuel to cease flowing through fuel filter unit 20 so that the contaminant draining operation may be commenced. In order to drain the system of contaminant, the user will first open vent port 28 by unscrewing screw-type valve 29 or otherwise opening the vent in order to release any vacuum that has built up inside fuel filter unit 20. The user will then open contaminant outlet port 36 on fuel filter lower unit 32, such as by unscrewing screw portion 39, whereby the contaminant present in contaminant collection zone 34 can be drained.

Upon draining of all of the contaminant out of contaminant collection zone 34, contaminant outlet port 36 and vent port 28 are both closed tightly. With the contaminant level now below the predetermined level of contaminant, the alarm conditions will cease and the user may then continue to cause fuel to enter contaminant detection apparatus 10 and engine E.

It will be understood that various details of the present subject matter may be changed without departing from the scope of the present subject matter. Furthermore, the foregoing description is for the purpose of illustration only, and not for the purpose of limitation, as the present subject matter is defined by the claims as set forth hereinafter.

What is claimed is:

1. An apparatus for detecting contaminant in a fuel system, the apparatus comprising:
   (a) a fuel filter comprising:
      (i) an upper unit having a fuel inlet port, a fuel outlet port, and a closeable vent port; and
      (ii) a lower unit releasably mounted to the upper unit and comprising a contaminant collection zone adapted for holding collected contaminant and a closeable contaminant outlet port adapted for draining the collected contaminant;
   (b) a programmable low-voltage variable contaminant detection sensor formed integrally within the upper unit of the fuel filter and comprising detection probes extending into the lower unit of the fuel filter for sensing contaminant levels within the contaminant collection zone, the sensor being adapted for generating a signal upon detection of a predetermined level of contaminant in the contaminant collection zone, wherein the sensor includes a microprocessor disposed within the upper unit and capable of varying the predetermined level to enable use with differently sized engines; and
   (c) at least one indicator for producing an alarm condition in response to receiving the signal from the contaminant detection sensor.

2. The apparatus of claim 1 wherein the contaminant to be detected is water.

3. The apparatus of claim 2 wherein the predetermined level of contaminant is programmed at a level of 20% water.

4. The apparatus of claim 1 wherein the upper fuel filter unit is constructed of a metal material and the lower fuel filter unit is constructed of a translucent material.

5. The apparatus of claim 4 wherein the translucent material is clear plastic.

6. The apparatus of claim 1 wherein the lower fuel filter unit is cylindrical.

7. The apparatus of claim 1 wherein the signal is an alarm signal.

8. The apparatus of claim 7 wherein the at least one indicator responding to the alarm signal comprises a visual indicator capable of producing a visual alarm condition.

9. The apparatus of claim 8 wherein the visual indicator is formed integrally within the upper unit of the fuel filter.

10. The apparatus of claim 7 wherein the at least one indicator responding to the alarm signal comprises an audible indicator capable of producing an audible alarm condition.

11. The apparatus of claim 1 wherein the fuel system is combined with an internal combustion engine.

12. The apparatus of claim 11 wherein the internal combustion engine is capable of operating on fuel selected from the group consisting of diesel and gasoline.

13. The apparatus of claim 1 wherein the fuel system is combined with a heating system.

14. An apparatus for detecting water in a fuel system of an internal combustion engine, the apparatus comprising:
   (a) a fuel filter comprising:
      (i) a metal upper unit having a fuel inlet port, a fuel outlet port, and a closeable vent port; and
      (ii) a translucent cylindrical lower unit releasably mounted to the upper unit and comprising a water collection zone adapted for holding collected water and a closeable water outlet port adapted for draining the collected water;
   (b) a programmable low-voltage variable water detection sensor formed integrally within the upper unit of the fuel filter and comprising detection probes extending into the lower unit of the fuel filter for sensing water levels within the water collection zone, the sensor being adapted for generating an alarm signal upon detection of a predetermined level of water in the water collection zone, wherein the sensor includes a microprocessor disposed within the upper unit and capable of varying the predetermined level to enable use with differently sized engines; and
   (c) indicators for producing an alarm condition in response to receiving the alarm signal from the water detection sensor wherein the indicators comprise a visual indicator capable of producing a visual alarm condition and an audible indicator capable of producing an audible alarm condition.

15. The apparatus of claim 14 wherein the predetermined level of water is programmed at a level of 20% water.

16. The apparatus of claim 14 wherein the lower fuel filter unit is constructed of clear plastic.

17. The apparatus of claim 14 wherein the internal combustion engine is capable of operating on fuel selected from the group consisting of diesel and gasoline.

18. A method of detecting contaminant in a fuel system of an internal combustion engine, the method comprising:
   (a) providing a contaminant detection apparatus comprising:
      (i) a fuel filter comprising an upper unit having a fuel inlet port, a fuel outlet port, and a closeable vent port and a lower unit releasably mounted to the upper unit and comprising a contaminant collection zone adapted for holding collected contaminant and a closeable contaminant outlet port adapted for draining the collected contaminant;
      (ii) a programmable low-voltage variable contaminant detection sensor formed integrally within the upper unit of the fuel filter and comprising detection probes extending into the lower unit of the fuel filter for sensing contaminant levels within the contaminant collection zone, the sensor being adapted for generating an alarm signal upon detection of a predetermined level of contaminant in the contaminant collection zone, wherein the sensor includes a microprocessor disposed within the upper unit and capable of varying the predetermined level to enable use with differently sized engines; and
      (iii) at least one indicator for producing an alarm condition in response to receiving the alarm signal from the contaminant detection sensor;
   (b) placing the contaminant detection system between a fuel source and the internal combustion engine;
   (c) programming the contaminant detection sensor with the predetermined level of contaminant desired for generation of the alarm signal;
   (d) causing fuel to enter the contaminant detection system from the fuel source;
   (e) monitoring the fuel and generating the alarm signal once the predetermined level of contaminant in the contaminant collection zone is reached;
   (f) indicating an alarm condition upon receipt of the alarm signal;
   (g) upon indication of the alarm condition, opening the upper unit vent port and the lower unit contaminant outlet port to cause draining of the collected contaminant; and
   (h) closing the upper unit vent port and the lower unit contaminant outlet port upon draining of all of the collected contaminant.

* * * * *

UNITED STATES PATENT AND TRADEMARK OFFICE
CERTIFICATE OF CORRECTION

PATENT NO. : 7,368,060 B2 Page 1 of 1
APPLICATION NO. : 11/035474
DATED : May 6, 2008
INVENTOR(S) : Michail Fachidis It is certified that error appears in the above-identified patent and that said Letters Patent is hereby corrected as shown below:

On the Title page correct the inventor information so that it reads as follows:

(75)　　Michail Fachidis

Signed and Sealed this

Nineteenth Day of August, 2008

JON W. DUDAS
*Director of the United States Patent and Trademark Office*